United States Patent [19]

Liboff et al.

[11] Patent Number: 5,267,939

[45] Date of Patent: * Dec. 7, 1993

[54] TECHNIQUES FOR CONTROLLING OSTEOPOROSIS USING NON-INVASIVE MAGNETIC FIELDS

[75] Inventors: Abraham R. Liboff, Birmingham, Mich.; Bruce R. McLeod, Bozeman, Mont.; Stephen D. Smith, Lexington, Ky.

[73] Assignee: Life Resonances, Inc., Bozeman, Mont.

[*] Notice: The portion of the term of this patent subsequent to Jun. 12, 2007 has been disclaimed.

[21] Appl. No.: 774,439

[22] Filed: Oct. 10, 1991

Related U.S. Application Data

[63] Continuation of Ser. No. 295,164, Jan. 9, 1989, Pat. No. 5,100,373.

[51] Int. Cl.$^5$ .............................................. A61N 1/00
[52] U.S. Cl. ........................................ 600/13; 600/15; 607/52
[58] Field of Search .................... 600/9, 13, 14, 15; 128/419 F, 424, 419 R, 421, 422, 799, 82.1

[56] References Cited

U.S. PATENT DOCUMENTS

| | | |
|---|---|---|
| 3,566,877 | 3/1971 | Smith et al. |
| 3,890,953 | 6/1975 | Kraus et al. |
| 3,893,462 | 7/1975 | Manning. |
| 3,911,930 | 10/1975 | Hagfors et al. |
| 3,915,151 | 10/1975 | Kraus .............. 128/419 F |
| 3,952,751 | 4/1976 | Yarger. |
| 4,066,065 | 1/1978 | Kraus .............. 128/419 F |
| 4,105,017 | 8/1978 | Ryaby et al. |
| 4,266,532 | 5/1981 | Ryaby et al. ........ 128/419 F |
| 4,315,503 | 2/1982 | Ryaby et al. ........ 128/419 F |
| 4,428,366 | 1/1984 | Findl et al. |
| 4,459,988 | 7/1984 | Dugot. |
| 4,467,808 | 8/1984 | Brighton et al. |
| 4,535,775 | 8/1985 | Brighton et al. |
| 4,548,208 | 10/1985 | Niemi .............. 128/419 F |
| 4,556,051 | 12/1985 | Maurer ............. 128/419 F |
| 4,600,010 | 7/1986 | Dugot. |
| 4,616,629 | 10/1986 | Moore. |
| 4,622,952 | 11/1986 | Gordon. |
| 4,622,953 | 11/1986 | Gordon. |
| 4,654,574 | 3/1987 | Thaler. |
| 4,683,873 | 8/1987 | Cadossi et al. |
| 4,757,804 | 7/1988 | Griffith et al. |
| 4,932,951 | 6/1990 | Liboff et al. ......... 128/419 F |
| 5,000,178 | 3/1991 | Griffith ............. 128/419 F |
| 5,014,699 | 5/1991 | Pollack et al. ....... 128/419 F |
| 5,038,780 | 8/1991 | Boetzkes ........... 128/419 F |
| 5,067,940 | 11/1991 | Liboff et al. ......... 128/419 F |
| 5,100,373 | 3/1992 | Liboff et al. ......... 128/419 F |
| 5,123,898 | 6/1992 | Liboff et al. ......... 128/419 F |
| 5,160,591 | 11/1992 | Liboff et al. ......... 128/419 F |

OTHER PUBLICATIONS

"Stimulation of Fracture Healing With Electromagnetic Fields of Extremely Low Frequency" (EMF of ELF) Clinical Orthopedics & Related Research, No. 186, Jun. 1984.

(List continued on next page.)

Primary Examiner—Randall L. Green
Assistant Examiner—K. M. Reichle
Attorney, Agent, or Firm—Dykema Gossett

[57] ABSTRACT

An apparatus and method for preventing and therapeutically treating osteoporosis are provided. The apparatus includes a magnetic field generator for producing a controlled, fluctuating, directionally oriented magnetic field parallel to a predetermined axis projecting through the target bone or skeletal system. In one aspect, a field detector samples the magnetic flux density along the predetermined axis and provides a signal to a microprocessor which determines the average value of the flux density. The applied magnetic field is oscillated at predetermined frequencies to maintain a preselected ratio of frequency to average flux density which controls osteoporosis. This ratio is maintained by adjusting the frequency of the fluctuating magnetic field and/or by adjusting the intensity of the applied magnetic field as the composite magnetic flux density changes in response to changes in the local magnetic field to which the target bone is subjected.

3 Claims, 4 Drawing Sheets

OTHER PUBLICATIONS

"Interactions Between Electromagnetic Fields and Cells" Chiabrera, et al., Plenum Publishing (1985), pp. 281–291.

"A Role for the Magnetic Field in the Radiation-Induced Efflux of Calcium Ions From Brain Tissue In Vitro" Bioelectromagnetics 6:327–337 (1985).

"Bioelectrochemical Studies of Implantable Bone Stimulation Electrodes" Bioelectrochemistry and Bioenergetics 5, 222–238 (1978).

"Inducing Bone Growth in Vivo by Pulse Stimulation" Clinical Orthopedics and Related Research, No. 88, Oct. 1972.

"Clinical Experiences with Low-Intensity Direct Current Stimulation of Bone Growth" Clinical Orthopedics and Related Research, No. 124, May 1977.

"Geomagnetic Cyclotron Resonance In Living Cells," Journal of Biological Physics, vol. 13, 1985.

TECHNIQUES FOR CONTROLLING OSTEOPOROSIS USING NON-INVASIVE MAGNETIC FIELDS

This is a continuation of copending application(s) Ser. No. 07/295,164 filed on Jan. 9, 1989, now U.S. Pat. No. 5,100,373.

FIELD OF THE INVENTION

The present invention relates generally to methods and apparatus for controlling osteoporosis. More specifically, the present invention discloses the use of non-invasive magnetic fields for the prevention and treatment of osteoporosis. The present invention also relates to a method for providing an animal model for the study of osteoporosis.

BACKGROUND OF THE INVENTION

It is known that in the bone disease, "osteoporosis," there is a decrease in bone density and an increase in bone porosity which significantly weakens the bone structure. More specifically, there is a progressive loss of bone mineral matrix, together with non-ossified material, such that the bones become thin and brittle. The weakened bone is susceptible to fracture upon even minor impact. While the exact etiology of osteoporosis is not fully understood, it is known that the demineralization of bone tissue is widespread throughout the skeletal system. As will be appreciated by those skilled in the art, in bone formation, osteoblasts and fibroblasts generate collagen which is then mineralized by calcium phosphate which, in turn, is converted to hydroxyapatite. It is also known that cells known as osteoclasts play an important role in the resorption of bone. Under normal conditions, bone remodeling, i.e. formation and resorption, occurs in coupled cycles to maintain equilibrium of bone mass. Bone also serves as a reservoir of calcium which is utilized in numerous cellular processes. It is believed that serum calcium regulation is mediated by the actions of parathyroid hormone, vitamin B, calcitonin, and various other local and systemic hormones. However, even if a detailed understanding of the pathways involved in bone remodeling remains unclear, it is apparent that the origin of osteoporosis is related to cell dysfunction as opposed to merely mineral imbalance.

A number of factors are known to increase an individual's predisposition to osteoporosis. It is a disease associated with aging, occurring somewhat later in men than in women. One of the most significant predisposing factors is the onset of menopause. A significant percentage of elderly women are afflicted with osteoporosis. It often leads to spinal compression fractures and collapse of vertebral bodies which may produce a dramatic change in posture. Long bone and hip fractures often lead to fatal complications. While estrogen replacement therapy has been attempted for the treatment of osteoporosis, its safety represents a problem and its efficiency is in question. Other pharmacologic treatments have also been attempted such as calcium, vitamin D and calcitonin supplements, but none have proved successful. Therefore, it would be desirable to provide a method and apparatus by which osteoporosis could be treated without the need for drug therapy.

The study of osteoporosis has been severely limited by the lack of an adequate animal model. The most popular animal model at this time is the limb disuse model in which the sciatic nerve of an experimental animal is severed to bring about disuse of the lower extremities. This disuse produces atrophy and weakened bone structures which have been assumed by some to be somewhat similar to the weakened bone structures present in osteoporosis, since both osteoporosis and disuse atrophy lead to reduced bone mass. However, differences between the two conditions exist, and the reliability of this model as a treatment for osteoporosis has been questioned. Therefore, it would be desirable to provide a reliable animal model which more precisely follows true osteoporosis.

Mechanical devices have been employed to counter the effects of osteoporosis. This approach assumes that skeletal homeostacis, the process by which the fractional bone mass in an individual is maintained, is a function of mechanical stress and physical exercise. Indeed, in younger individuals, as well as in animals, it is known that decreased mechanical stress, as seen in disuse, immobilization, and most dramatically in astronauts in space flight, is related to increased bone resorption. However important this type of bone loss may be in younger individuals exposed to prolonged weightlessness in low-gravity environments, in bed-ridden immobilizations, or experimental animal models involving disuse atrophy, it remains clear that the onset and continuation of osteoporosis in older individuals is marginally connected, if at all, to exercise habits and is not reversible with programs of exercise.

In recent years, multidisciplinary investigations of developmental processes have provided evidence suggesting that electric and magnetic fields play an important role in cell and tissue behavior. In U.S. patent application Ser. No. 923,760, entitled, "Techniques for Enhancing the Permeability of Ions," which has been assigned to the assignee of the present invention and the disclosure of which is incorporated herein by reference, a method and apparatus are disclosed by which transmembrane movement of a preselected ion is magnetically regulated using a time-varying magnetic field. The fluctuating magnetic field is preferably tuned to the cyclotron resonance energy absorption frequency of the preselected ion. This important discovery brought to light the interplay of local geomagnetic fields and frequency dependence in ion transport mechanisms. It has now been discovered that by utilizing and extending the principles of cyclotron resonance tuning, an unexpected and remarkable advance in the control and modification of developmental processes in living tissue can be achieved. In U.S. patent application Ser. No. 172,268 filed Mar. 23, 1988, the inventors of the present invention disclose that cyclotron resonance can be used to control tissue development. In U.S. patent application entitled "Method and Apparatus For Controlling the Growth of Non-Osseous, Non-Cartilaginous, Solid Connective Tissue," filed Oct. 6, 1988, U.S. Ser. No. 254,438, the present inventors disclose a method of controlling the growth of non-osseous, non-cartilaginous, connective tissue which utilizes cyclotron resonance frequencies.

Still other art devices which broadly relate to non-invasive tissue control are typified by the devices disclosed in U.S. Pat. No. 3,893,462 to Manning entitled, "Bioelectrochemical Regenerator and Stimulator Devices and Methods for Applying Electrical Energy to Cells and/or Tissue in a Living Body" and in U.S. Pat. No. 4,105,017 to Ryaby et al. entitled, "Modification of the Growth Repair and Maintenance Behavior of Living Tissue and Cells by a Specific and Selective Change in Electrical Environment." These investigators have focused on the use of large pulsed magnetic fields to produce moderately high induced currents in living tissue with well-defined "therapeutic" waveforms. In U.S. Pat. No. 4,467,808 to Brighton, a non-invasive method of treating osteoporosis is disclosed which uses AC electrodes and high-frequency currents. It should also be noted that although a possible role of magnetic fields beyond the galvanic action of induced currents is briefly mentioned in U.S. Pat. No. 3,890,953 to Kraus et al., to Applicants' knowledge no investigator has previously controlled osteoporosis in the manner set forth in the present invention.

SUMMARY OF THE INVENTION

In one aspect, the present invention provides an apparatus for controlling osteoporosis. The inventive method and apparatus can be used to prevent the onset of osteoporosis, delay the progression of osteoporosis, or reverse the effects of osteoporosis. The novel apparatus includes magnetic field generating means such as a field coil for generating a controlled, fluctuating magnetic field which penetrates bone tissue in a human or animal subject. In one aspect, the apparatus of the present invention is designed for the topical or localized treatment of bone and preferably includes a magnetic field sensing device for measuring the intensity of the magnetic field present at the target bone. In another aspect, the apparatus of the present invention is designed for the systemic treatment of osteoporosis.

In one embodiment of the topical treatment apparatus, the magnetic field generating means and magnetic field sensor are enclosed within a housing along with a power source such as a battery or the like. In operation, the magnetic field generating means is positioned adjacent to a region of bone tissue to be treated for osteoporosis. A fluctuating, directional magnetic field is then generated by the magnetic field generating means. The applied magnetic flux density is directed along a predetermined axis which passes through the bone to be affected. In one embodiment, the applied magnetic flux density along the axis is superimposed on that component of the local or ambient magnetic field which is parallel to the predetermined axis to create a fluctuating composite field. The resultant combined magnetic flux density which is parallel to the predetermined axis and which passes through the bone is measured by the magnetic field sensor. The magnetic field sensor determines the net average value of the magnetic flux density which passes through the target bone tissue along the predetermined axis. In one embodiment, the frequency of the fluctuating magnetic field is set at a predetermined value and the net average value of the magnetic flux density is then regulated by adjusting the magnitude of the applied magnetic field to produce a combined magnetic field having a preselected ratio of frequency-to-field magnitude which is effective in the prevention and therapeutic treatment of osteoporosis.

In a preferred embodiment, changes in the magnitude of the local magnetic field along the predetermined axis which would otherwise alter the magnetic flux density of the combined magnetic field parallel to the predetermined axis and which would thus produce a deviation from the desired ratio are counterbalanced by adjustment of the magnitude of the applied, fluctuating magnetic field. This adjustment is preferably made by microprocessing means in association with both the magnetic field generating means and the magnetic field sensor. Preferred ratios of frequency-to-field magnitude are determined with reference to the equation:

$$f_c/B = q/(2\pi m)$$

where $f_c$ is the frequency of the combined magnetic field in Hertz, B is the non-zero average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla. In one embodiment, the values of q and m are selected with reference to the charge and mass of a preselected ion.

In another embodiment, changes in the ambient magnetic field which would otherwise alter the ratio of frequency-to-magnetic field are counterbalanced by adjusting the frequency of the applied magnetic field to maintain the preferred ratio. The present invention also contemplates the adjustment of both frequency and field magnitude to maintain the predetermined preferred ratio. Preferably, the peak-to-peak amplitude of the AC component is in the range of about $2.0 \times 10^{-7}$ to about $2.0 \times 10^{-4}$ Tesla. The waveform is preferably substantially sinusoidal, but other waveforms may be suitable.

In another embodiment the present invention provides an apparatus for the systemic control of osteoporosis which includes an enclosure in which a patient to be treated is positioned. The enclosure includes a large solenoid which is utilized for generating a magnetic field having the aforementioned therapeutic characteristics. The solenoid generates this magnetic field in a manner in which a substantial portion of the subject is exposed uniformly to the field.

The present invention also provides a method of topically treating osteoporosis which includes in one aspect the steps of generating a fluctuating, directionally-oriented magnetic field; positioning a region of bone of a human or animal subject within the fluctuating, magnetic field so that the field passes through the bone parallel to a predetermined axis that extends through the bone; measuring the net average value of the combined magnetic flux density parallel to the predetermined axis through the bone, where the combined magnetic field is the sum of the local magnetic field along the predetermined axis and the applied magnetic field; adjusting the frequency and/or magnitude of the applied magnetic field to produce a combined magnetic field along the axis having a predetermined ratio of frequency-to-magnitude, where the predetermined ratio is effective in treating osteoporosis; maintaining the predetermined ratio of frequency to magnitude of the combined field; and exposing the bone to the combined magnetic field for a period of time sufficient to bring about the desired prevention treatment of osteoporosis. Other relationships between frequency and magnitude may be useful or even desirable in a particular application.

In still another aspect, the present invention provides a method for the systemic therapeutic treatment of osteoporosis which comprises placing a subject inside an enclosure equipped with a solenoid; generating a fluctuating, directionally-oriented magnetic field utilizing the solenoid wherein the magnetic field penetrates substantially all of the skeletal tissue of the subject; measuring the net average value of the combined magnetic flux density parallel to a predetermined axis which passes through the subject, where the combined magnetic field is the sum of the local magnetic field along the predetermined axis and the applied magnetic field; adjusting the frequency and/or magnitude of the applied magnetic field to produce a combined magnetic field along the axis having a predetermined ratio of frequency-to-magnitude, where the predetermined ratio is effective in preventing or therapeutically treating osteoporosis; maintaining the predetermined ratio of frequency to magnitude of the combined field; and exposing the subject to the combined magnetic field for a period of time sufficient to bring about the desired prevention or treatment of osteoporosis.

In another aspect, the present invention provides a method for producing a non-human animal model for the study of osteoporosis. Accordingly, in one aspect, an experimental animal is placed inside an enclosure equipped with a solenoid; a fluctuating, directionally-oriented magnetic field is generated utilizing the solenoid wherein the magnetic field penetrates substantially all of the skeletal tissue of the experimental animal; measuring the net average value of the combined magnetic flux density parallel to a predetermined axis which passes through the experimental animal, where the combined magnetic field is the sum of the local magnetic field along the predetermined axis and the applied magnetic field; adjusting the frequency and/or magnitude of the applied magnetic field to produce a combined magnetic field along the axis having a predetermined ratio of frequency-to-magnitude, where the predetermined ratio is effective in creating an osteoporotic-like condition in the experimental animal; maintaining the predetermined ratio of frequency to magnitude of the combined field; and exposing the experimental animal to the combined magnetic field for a period of time sufficient to bring about the osteoporotic-like condition. Alternatively, a localized osteoporotic-like condition is created in an experimental animal by topical treatment as will be more fully explained.

DETAILED DESCRIPTION OF THE PREFERRED EMBODIMENTS

Figure 1:
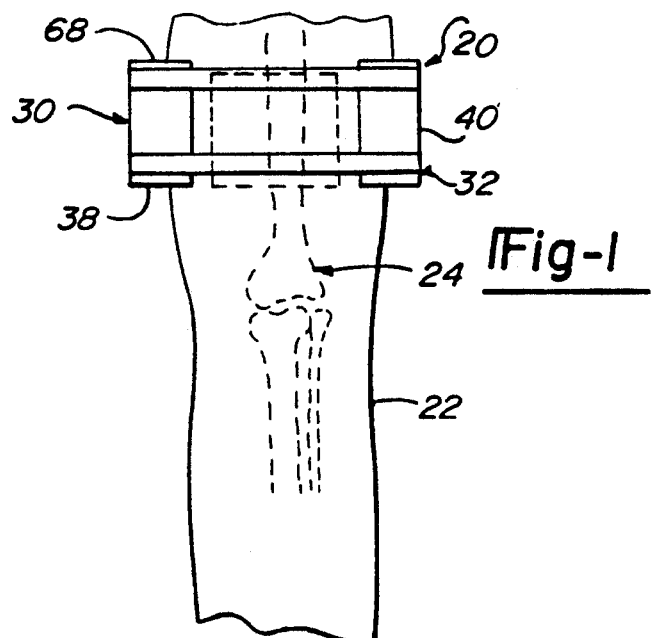
FIG. 1 is a front elevational view of the present invention as applied to the topical treatment of osteoporosis.

Referring now to FIG. 1 of the drawings, treatment apparatus 20 is shown in position on leg 22 of a human subject. It is to be understood that both the apparatus and the method of the present invention are for use in the prevention and therapeutic treatment of osteoporosis in living bone tissue of man or similar conditions of decreased bone density in animals. Thus, in one embodiment of the present invention the target tissue which is to be treated in accordance with the present invention is a region of bone. As used herein, the term "bone," "bone tissue" or the like shall be defined, without limiting its customary meaning, as bone which is capable of undergoing bone formation processes. This will include both the formation of a collagen matrix as well as the mineralization of the matrix. Although the stimulation of bone formation or the prevention of bone resorption will be emphasized herein, the present invention is also useful to produce an animal model for the study of osteoporosis by stimulating osteoporosis and bone resorption in an experimental animal.

Femur 24 is shown which will receive in this embodiment topical therapeutic treatment for osteoporosis in accordance with the present invention. Accordingly, treatment apparatus 20 includes two treatment heads 30 and 32 which are positioned on leg 22 in the region to be treated in the opposed fashion illustrated in FIG. 1. As will be explained more fully, it is important that treatment heads 30 and 32 be placed adjacent to the bone such that the bone is within the range of the magnetic flux generated by the treatment heads. Since the magnetic fields penetrate the surrounding soft tissues, non-invasive treatment is made possible. Also, although it is preferred that two treatment heads be employed in an opposed fashion as illustrated in FIG. 1, a single treatment head, a plurality of treatment heads greater than two, or a single solenoid through which a limb is inserted may be suitable for topical treatment may be suitable in some applications.

Figure 2:
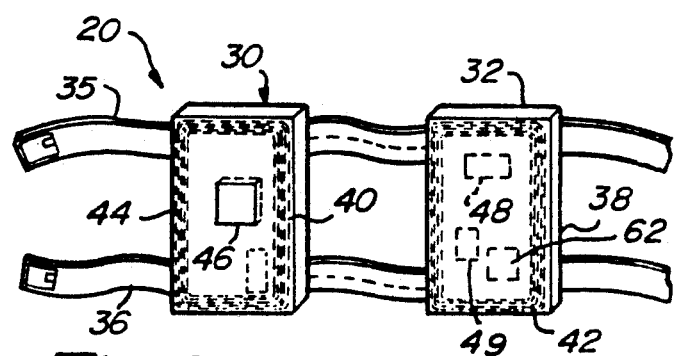
FIG. 2 is a front elevational view of the present invention for topical treatment with two treatment heads having field coils and magnetic field sensing means shown in phantom.

Referring now to FIG. 2 of the drawings, retaining straps 34 and 36 are seen by which treatment apparatus 20 is preferably secured into position on leg 22. Other securing means may be suitable or desirable in a particular application. It may also be desirable to provide treatment apparatus 20 as a stationary unit or the like as an alternative to the mobile unit depicted in FIGS. 1–3. Straps or belts 34 and 36 are attached to treatment heads 30, 32 by any convenient means, preferably in a manner which allows the distance between treatment heads 30, 32 to be adjusted to be obtain the substantially opposed orientation shown in FIG. 1. Hence, it is preferred that straps 30, 32 permit adjustment sufficient for treatment apparatus 20 to be used on limbs of various sizes. Since osteoporosis often afflicts other parts of the skeletal system such as the pelvis and vertabrae, other configurations of treatment apparatus 20 may by necessary in some applications. Treatment heads 30 and 32 should be snugly but comfortably in position to prevent substantial movement relative to the bone region to treated.

Figure 3:
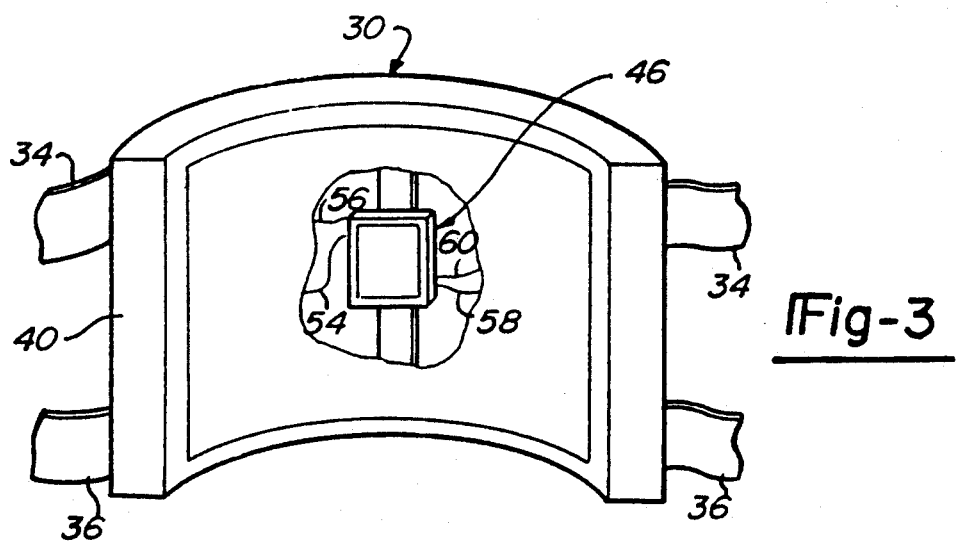
FIG. 3 is a front elevational view of one treatment head of the present invention with the housing broken away to illustrate the magnetic field sensing means.

Referring now to FIGS. 2 and 3, each treatment head 30, 32 includes a housing 38, 40 of a non-magnetic material such as plastic which encloses a field coil 42, 44. In addition, it is preferred that at least one treatment head enclose a magnetic field sensing device 46, such as a Hall-effect device, shown enclosed within housing 40 of treatment head 30. Power source 48 is provided, preferably enclosed within one of the treatment heads. Power source 48 may comprise a dry cell battery or the like. It is preferred that two or more separate power sources be provided to minimize the number of circuit elements required. Housing 38 is also preferably provided with means by which battery 48 can be accessed such as a sliding panel or the like (not shown) to facilitate installation. It may also be suitable to mount battery 48 on the outside of housing 38 or to provide some other external arrangement. While it is a significant feature and advantage of the present invention to provide a treatment apparatus which includes a self-contained power source, and thus which is both lightweight and mobile, other power sources such as an ac line source may be used in connection with an ac/dc converter where mobility is not required.

Field coils 44 and 42 are the preferred means by which an applied magnetic field is generated for topical or local treamtment of a region of bone afflicted with osteoporosis in the present invention. The radius of each field coil 44 and 42, as well as the turns of winding, may vary in accordance with the principles of the present invention. Those skilled in the art will appreciate that other electromagnets or possibly permanent magnets may be adapted for use in the present invention and any such use is intended to come within the scope of the present invention. Field coils 44 and 42 are most preferred since they provide a simple means for concentrating magnetic lines of force. Also, the present invention includes several components within a single housing, and therefore shielding may be employed to prevent undesired interactions between components.

Figure 4:
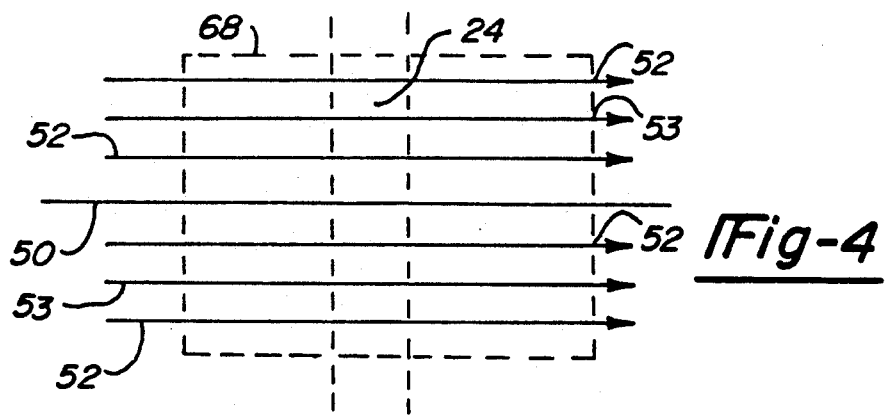
FIG. 4 illustrates the combined magnetic flux.

In the most preferred arrangement, the geometry and relative position of field coils 44, 42 during treatment are such that field coils 44, 42 operate as Helmholtz coils. Those skilled in the art will thus appreciate that in the most preferred arrangement, field coils 44, 42 are substantially identical, field-aiding, parallel coaxial coils separated by a distance equal to the radius of each coil. In this most preferred embodiment, the Helmholtz configuration produces an applied magnetic field in a predetermined space between the coils. Referring to FIG. 4, this predetermined space 68 is occupied by the region of bone to be treated. This concept will be more fully explained herein. Hence, predetermined space 68 is shown through which magnetic field lines 52 extend parallel to predetermined axis 50. Magnetic field lines 52 pass through the target bone, which is illustrated here as femur 24.

It will be appreciated that the target bone will generally be subject to local magnetic influences. As used herein, "local magnetic field" shall be defined as the magnetic influences, including the earth's magnetic field or geomagnetic field, which create a local magnetic flux that flows through the target bone. "Magnetic flux density" shall be defined in the customary manner as the number of magnetic field lines per unit area through a section perpendicular to the direction of flux. Factors contributing to the local magnetic field in addition to the geomagnetic field may include localized regions of ferromagnetic materials or the like. In one embodiment of the present invention, field coils 42 and 44 are used to create an applied, fluctuating magnetic field which when combined with the local magnetic field parallel to predetermined axis 50 produces a resultant or combined magnetic field having a precisely controlled, predetermined ratio of magnetic flux density to frequency.

Referring now again to FIG. 3 of the drawings, magnetic field sensing device or magnetometer 46 is shown in housing 40 with the appropriate leads 54, 56, 58 and 60, by which the field-sensing device is electrically connected to power source 48 and in one embodiment to microprocessing means 62. As will be appreciated by those skilled in the art, the Helmholtz configuration of field coils 42, 44 provides a substantially uniform or equal applied magnetic field in active volume or predetermined space 68 between the coils. Hence, treatment apparatus 20 allows a substantially uniform applied magnetic field to be applied to the target tissue in predetermined space 68. The direction of the applied magnetic flux defines the direction of predetermined axis 50. That is, the flux of the applied magnetic field is always in the same direction as predetermined axis 50. In one preferred embodiment of the invention, this applied magnetic flux is superimposed on the local magnetic flux in predetermined space 68. The field lines of this local flux component are shown by reference numeral 53 in FIG. 4.

Magnetometer 46 is positioned in treatment apparatus 20 to measure the total or composite magnetic flux which passes through predetermined space 68 parallel to predetermined axis 50. It will be understood, then, that magnetometer 46 is provided to measure the composite magnetic field along axis 50. The local field component either augments or decreases the applied magnetic flux unless the local field component is zero. This is an important feature of the present invention. The relatively low applied flux densities and precise predetermined relationships of combined flux density and frequency provided by the present invention must be maintained during treatment, notwithstanding the influence of the local magnetic field. This is achieved in essentially two preferred manners which will be explained more fully herein. Thus, magnetometer 46 is provided to determine the magnitude of the magnetic flux density of the local magnetic field. Hence, in one embodiment of the invention, predetermined space 68 is occupied by a region of living bone of a human or animal subject. Predetermined axis 50 which projects through predetermined space 68 and thus through the target bone region is defined by the relative position of treatment apparatus 20 with respect to the bone. Predetermined axis 50 is in the same direction as the applied magnetic flux generated by field coils 42, 44 through predetermined space 68. During this procedure, magnetometer 46 measures the total magnetic flux density parallel to predetermined axis 50 which passes through the target tissue. This total or composite magnetic flux density is the sum of the applied component and the local component. The local component may at times be in the same direction as the applied flux and at other times be in directions other than the applied flux. At times the local component may also be zero. These changes in the local component along the axis are produced by changes in the direction of predetermined axis 50 as treatment apparatus 20 is repositioned such as when an ambulatory subject receiving treatment moves leg 22. Thus at $T_1$ the applied flux generated by field coils 42, 44 may be parallel to a north-south axis, perhaps when the subject faces west. Since the direction of predetermined axis 50 is defined by the direction of the applied flux, in this position, predetermined axis 50 is therefore also in the north-south direction. At $T_2$, the subject may turn to the north causing a 90 degree rotation of field coils 42, 44 such that the applied magnetic flux is now parallel to an east-west axis. Accordingly, predetermined axis 50 is then also in the east-west direction. In most cases, the local component will be different in different directions; hence, the composite flux measured by magnetometer 46 along predetermined axis 50 will change in response to changes in the position of treatment apparatus 20 with respect to the local magnetic field. The net average value of magnetic flux density is accordingly regulated to adjust to the change in composite flux. Therefore, in this embodiment of the present invention which is designed for the local treatment of a region of bone, treatment apparatus 20 is preferably a mobile unit which is a significant advantage.

Figure 5:
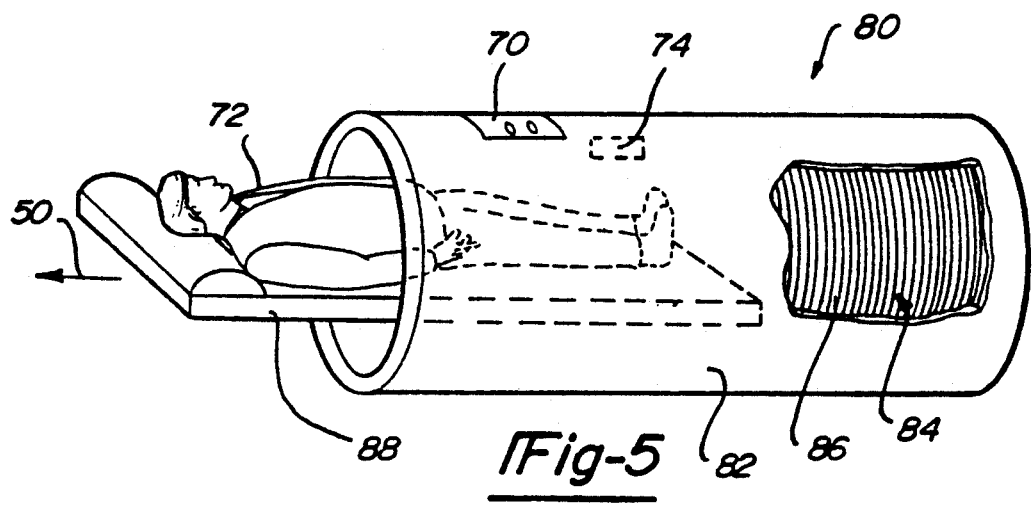
FIG. 5 is a perspective view of the present invention for use in systemic treatment of osteoporosis.

In another aspect the present invention provides an apparatus for the systemic prevention and therapeutic treatment of osteoporosis. By "systemic treatment" it is meant that substantially all of the subject's skeletal system is simultaneously exposed to the therapeutic magnetic fields in accordance with the present invention. Accordingly, and referring now to FIG. 5 of the drawings, systemic treatment apparatus 80 is shown which comprises a tube or cylinder 82 of a non-magnetic material such as plastic. Tube 82 houses a large solenoid 84 which contains multiple turns of wire 86 and which extends substantially the entire length of systemic treatment apparatus 80. Gurney or platform 88 is provided on a track system (not shown) which allows platform 88 to move between a first position outside of tube 82 to a second position inside of tube 82. A controller 70 is provided along with the necessary circuitry for energizing solenoid 84 to create a magnetic field in the direction of axis 50, which in this embodiment projects through the central bore of solenoid 84. In other words, and as will be appreciated by those skilled in the art, the magnetic flux generated by solenoid 84 will run through the center of the coil. Patient 72 is placed on platform 88 and platform 88 is then moved into position inside tube 82. Thus patient 72 is positioned inside solenoid 84 with the applied magnetic flux penetrating the patient's entire body in the direction of predetermined axis 50. In one embodiment a magnetic field sensor 74 is also provided to measure the magnetic flux density along axis 50 and may be mounted on a track system within tube 82. It may be suitable in some applications to mount tube 82 on a rotatable stand such that tube 82 can be rotated to change the position of patient 72 and axis 50 with respect to the local magnetic field. Other configurations of systemic treatment apparatus 80 may be suitable or even desirable in a particular application such as large flat coils (for example having diameters of six feet or greater) in Helmhotz arrangement with one coil being placed on each side of patient 72. In this alternative arrangement, axis 50 would extend transverse to the patient's body rather than from toe-to-head as shown in FIG. 5. Of course, the direction of the magnetic field may also be directly opposite to the direction of axis 50 depending upon the direction of current through solenoid 84.

Figure 6:
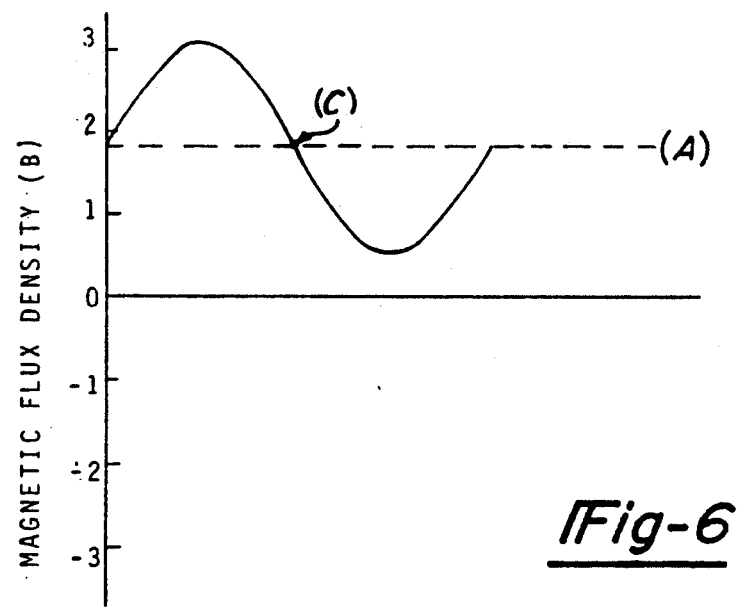
FIG. 6 illustrates the fluctuating, non-zero average value of the combined magnetic flux density.

The unexpected and superior results of the present invention are achieved by treatment apparatus 20 and system treatment apparatus 80 by creating a fluctuating combined or composite magnetic field having a magnetic flux density parallel to predetermined axis 50, where the combined magnetic flux density along axis 50 is maintained at a predetermined relationship to the frequency of the fluctuations. In this embodiment, the combined magnetic flux density parallel to predetermined axis 50 has a non-zero net average value. As illustrated in FIG. 6 of the drawings, the therapeutic magnetic field of the present invention can be thought of as a static field having reference level A on which a fluctuating magnetic field is superimposed. It comprises an ac component which varies in amplitude but not direction and a dc reference around which the ac component varies. Reference level A is the non-zero average value of the flux density (B). Therefore, it will be understood that the non-zero average or net average value of the composite magnetic flux density along predetermined axis 50 is utilized since the magnitude B of the composite flux density changes at a predetermined rate due to oscillation or fluctuation of the applied magnetic flux. Thus, an average value is utilized which is a non-zero average value illustrated at point (c). This reflects that although the composite magnetic flux density along the axis is oscillating at a controlled rate, the composite field is regulated by the intensity of the applied field to ensure that the composite field is always unipolar; that is, the composite field is always in the same direction along predetermined axis 50. In those instances where full wave rectification is utilized to generate the applied magnetic field (as more fully explained in the aforementioned U.S. patent application Ser. No. 923,760 of Oct. 27, 1986 which is incorporated herein by reference) the rms value is the non-zero average value.

As stated, it has been found that rather precise relationships of the flux density of the combined magnetic field to the frequency of the fluctuations are used in the present invention to provide therapeutic results. These ratios of frequency to composite flux density are found in accordance with the following equation:

$$f_c/B = q/(2\pi m)$$

where $f_c$ is the frequency of the combined magnetic field in Hertz, B is the net average value of the magnetic flux density of the combined magnetic field parallel to predetermined axis 50 in Tesla, q/m has a value of from about $5 \times 10^5$ to about $100 \times 10^6$ Coulombs per kilogram. B preferably has a value not in excess of about $5 \times 10^{-4}$ Tesla. To prevent and therapeutically treat osteoporosis, the following frequency and associated combined magnetic flux density (B) is preferred:

| fc (Hertz) | B (Tesla) |
| --- | --- |
| 16.0 | $12.68 \times 10^{-6}$ | at an ac amplitude, peak-to-peak of 15 microTesla rms. Another preferred relationship is:

| fc (Hertz) | B (Tesla) |
| --- | --- |
| 30.0 | $39.2 \times 10^{-6}$ | at an ac amplitude, peak-to-peak of 15 microTesla rms.

While the exact mechanism by which osteoporosis is prevented and/or treated by the present invention is not fully understood, as will be explained more fully in connection with the method of the present invention, remarkable results are achieved by tuning the combined field to resonant absorption frequencies of preselected ions as will be more fully explained hereinafter. This is true for both the topical prevention and treatment of osteoporosis with treatment apparatus 20 and for the systemic prevention and treatment of osteoporosis with systemic treatment apparatus 80.

Therefore, it will be readily understood by those skilled in the art that in one embodiment treatment apparatus 20 includes in one aspect a magnetic field generating means for providing an oscillating magnetic field parallel to a predetermined axis. Treatment apparatus 20 also preferably includes magnetic field sensing means by which the magnetic flux density parallel to the predetermined axis is measured. A microcontrolling means is also preferably provided in treatment apparatus 20 by which a predetermined relationship between the magnetic flux density parallel to the predetermined axis and the frequency of the magnetic field oscillation is created and maintained as treatment apparatus 20 changes orientation with respect to the local magnetic field. Treatment apparatus 20 is thus used to create, monitor and adjust a magnetic field of predetermined parameters in predetermined volume 68. While this predetermined relationship is preferably maintained by adjusting the applied flux to compensate for changes in the local field component, alternatively, the frequency can be adjusted to preserve the desired ratio. In that embodiment adapted for systemic treatment, systemic treatment apparatus 80 is provided which includes in one aspect a magnetic field generating means for providing an oscillating magnetic field parallel to predetermined axis 50. Systemic treatment apparatus 80 also preferably includes a platform on a track which allows a patient to be positioned within the central bore of a large solenoid. Systemic treatment apparatus also preferably includes magnetic field sensing means by which the magnetic flux density parallel to the predetermined axis is measured. Systemic treatment apparatus 80 is thus used to create a magnetic field of predetermined parameters inside tube 82 (a region which corresponds to predetermined space or volume 68). While this predetermined relationship is preferably maintained by adjusting the applied flux to compensate for changes in the local field component, alternatively, the frequency can be adjusted to preserve the desired ratio.

In use, for topical application, a region of bone in a living subject such as a human in which it is desired to prevent or treat osteoporosis is placed within predetermined volume 68 and is then subjected to a fluctuating magnetic field as described for a period of time sufficient to bring about the desired treatment. It is believed that exposure in accordance with the present invention of about 500 hours or more brings about some beneficial results in the treatment and/or prevention of osteoporosis. While the length of time necessary for successful treatment may vary, it is anticipated that up to about 100 days of treatment will provide beneficial results. Longer treatment or regular, periodic treatments over long periods of time may be desirable in the prevention of osteoporosis. In applications to prevent bone loss due to environmental conditions, as for astronauts or bedridden patients, continuous treatment may be required, with suitable revisions in the mode of application to suit these different conditions.

For systemic treatment, patient 72 is placed on platform 88 which is then moved into position within tube 82 and thus within solenoid 84. Patient 72 is then subjected to a fluctuating magnetic field, as previously described, for a period of time sufficient to bring about the desired systemic treatment. It is believed that exposure in accordance with the systemic treatment embodiment of the present invention of about 500 hours or more brings about some beneficial results in the treatment and/or prevention of osteoporosis. While the length of time necessary for successful treatment may vary, it is anticipated that up to about 100 days of treatment will provide beneficial results. Longer treatment may be desirable in the prevention of osteoporosis in some applications.

In another embodiment of the present invention, values for q and m are determined with reference to a preselected ionic species. It will be known by those skilled in the art that numerous ions are in the biological fluids associated with bone tissue and cells. These ions include potassium ions, magnesium ions, sodiums ions, chloride ions, phosphate ions, sulfate ions, carbonate ions, bicarbonate ions and the like and various ions formed by the dissociation of amino acids, proteins, sugars, nucleotides and enzymes. Applicants have found that by utilizing the values of charge and mass for a preselected ion in the equation set forth above, which will be recognized by those skilled in the art as the cyclotron resonance relationship solved for $f_c/B$, ratios of frequency to magnetic flux density can be determined which serve to prevent or therapeutically treat osteoporosis in accordance with the present invention. By using the charge-to-mass ratio of a preselected ion, a specific cyclotron resonance frequency for the ion can be determined. By then tuning treatment apparatus 20 or systemic treatment apparatus 80 to maintain a combined magnetic flux density having the proper cyclotron resonance frequency, prevention of osteoporosis and therapeutic treatment of osteoporosis can be achieved by restoring or enhancing cell function in those cells which normally act to control bone remodeling. Evidence indicates that the beneficial results of the present invention in this embodiment are achieved when the preselected ion absorbs energy from the magnetic field of the present invention having the desired parameters. For the prevention and treatment of osteoporosis, it is preferred that the preselected ion to which the apparatus is tuned comprise $Ca^{++}$ or $Mg^{++}$. Harmonics of these values may also be suitable.

It will be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field within volume 68 (substantially the entire region or volume within tube 82 in the systemic treatment apparatus) which has the desired characteristics. However, as stated, it is preferred to maintain a constant frequency which thus requires that the intensity of the applied magnetic flux density be adjusted to compensate for changes in the local magnetic field in order to maintain a constant ratio of frequency to magnetic flux density. For example, if it necessary to maintain a frequency of 16 Hz and an average flux density of $1.26 \times 10^{-5}$ Tesla to prevent or treat osteoporosis, changes in the local field which would otherwise cause unwanted deviations in the combined magnetic flux density must be corrected by increasing or decreasing the applied magnetic flux density accordingly. In the case of systemic treatment apparatus 60, since the apparatus is stationary in one embodiment, this correction is generally not necessary. Adjustment is most preferably performed by the microcontroller in connection with both the field generating means and the field-sensing device. Alternatively, as stated, if changes in the combined magnetic flux density along the axis occur due to changes in the orientation of treatment apparatus 20 with respect to the local magnetic field, the frequency of the oscillation can then be changed so that the preferred therapeutic ratio is maintained. Once again, it is important to realize that the value of B is the average composite magnetic flux density parallel to the predetermined axis since the magnitude of the flux density changes as the field is oscillated. It will be understood that detection of changes in the magnetic field due to changes in the ambient component should be at intervals frequent enough to provide a frequency-to-magnetic field ratio which is substantially constant, notwithstanding the changes in the local field component.

Each field coil 42, 44 preferably has up to about 3000 turns or loops of conducting wire, the diameter d of each loop being preferably up to about 300 centimeters. The number of turns of wire n, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention.

It is also to be understood that the applied magnetic field which results in a combined magnetic flux density along predetermined axis 50 may be produced by a sinusoidal signal or by other methods such as a full-wave rectified signal applied to field coils 42, 44 or solenoid 84. It may also be appropriate in some instances to reduce components of the local magnetic field which are not parallel to predetermined axis 50 to zero through the use of additional coils positioned at right angles to treatment heads 30, 32 to create an opposite but equal field.

Figure 7:
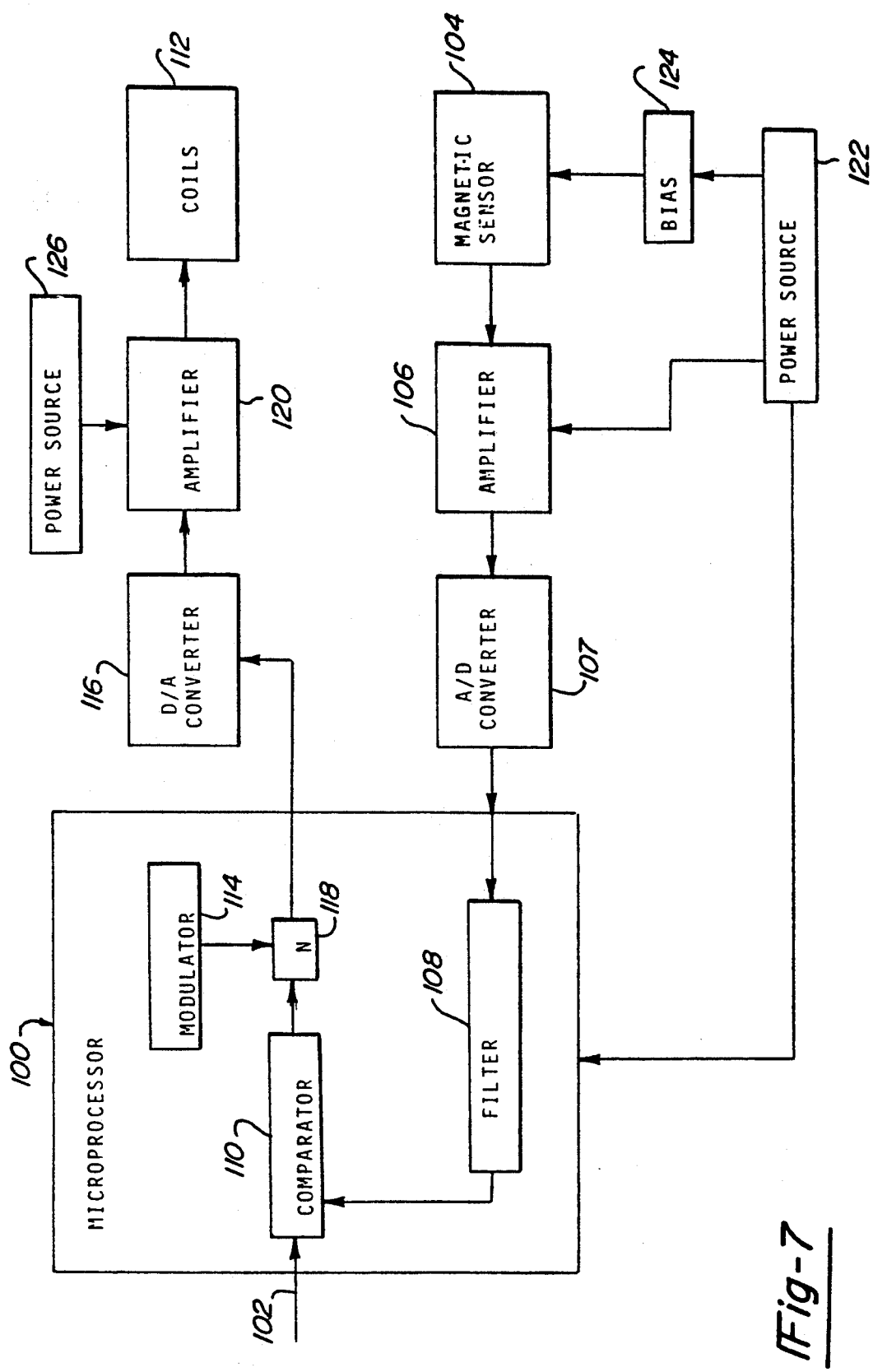
FIG. 7 is a block diagram of an embodiment of the present invention in which the circuit of the inventive apparatus is arbitrarily divided into convenient functional sections.

Referring now to FIG. 7 of the drawings, a block diagram is shown which depicts one preferred arrangement of the circuits of treatment apparatus 20 in functional segments. Numerous other circuit arrangements may be possible if the principles of the present invention are faithfully observed. Microcontroller or microprocessor 100 is seen by which the composite magnetic field is maintained at a constant predetermined level despite changes in the ambient component as previously described. In this respect, input 102 is provided by which a set point value of the predetermined composite magnetic flux density along a predetermined axis through the target tissue is input into microprocessor 100. As will be shown, the composite field strength is compared to this set point value to generate an error equal to the difference in the set point value and the measured value of the composite magnetic flux density along the axis.

Magnetic field sensor 104 is provided by which the magnitude of the composite field which passes through the target tissue along the axis is measured. It is preferred that magnetic field sensor 104 comprise a Hall-effect device which, as will be known by those skilled in the art, produces an analog signal. The magnetic field sensor 104 constantly monitors the composite magnetic field, sending a signal to microprocessor 100. It will be understood that the output of a Hall-effect magnetic sensor is relatively small; thus, magnetic field sensor amplifier 106 is provided by which the signal from magnetic field sensor 104 is amplified, for example, up to three thousand times its original value. Since a Hall-effect device produces an analog signal, analog-to-digital converter 107 is provided by which the amplified signal from magnetic field sensor 104 is converted to a digital signal which can be used by microprocessor 100. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital convertor 106 which is input into microprocessor 100 is filtered by software filter 108 to remove shot noise and sudden fluctuations in the composite field detected by magnetic field sensor 104. Although it is preferred that filter 108 comprise software in microprocessor 100, a discrete filter could be used. In this embodiment, software filter 108 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more which result primarily from changes in the orientation of treatment apparatus 20 with respect to the ambient field component. Hence, the time constant of filter 108 should be such that momentary fluctuations are filtered out.

Microprocessor 100 includes logic which calculates the non-zero net average value of the composite magnetic flux density. This non-zero average value is then compared at comparator 110 in microprocessor 100 to the predetermined dc reference or offset value which is input into microprocessor 100 via input 102. It should be noted that this reference value is preferably established by dedicated circuitry in microprocessor 100, although variable inmput means could be included by which the set point value could be changed. An error statement is then generated defining the difference in the measured value of the composite magnetic flux density and the set point or reference value. Microprocessor 100 then determines the magnitude of the output necessary to drive magnetic field generating coils 112 to bring the composite magnetic flux density back to the set point.

Software field modulator or oscillator 114 is provided by which an ac or fluctuating component is superimposed on the digital output signal which is input into digital-to-analog converter 116. From the previous discussion of the present invention, it will be understood that software field modulator 114 of microprocessor 100 in the preferred embodiment of the present invention is preset to a fixed, predetermined frequency to produce the desired predetermined, ratio of frequency-to-magnetic flux density value for preventing or treating osteoporosis. In another embodiment, the feedback system of the present invention is such that changes in the composite magnetic flux density are measured, whereupon microprocessor 100 determines the necessary change in frequency to maintain the predetermined relationship. In that embodiment, software field modulator 114 produces the requisite ac frequency. It is again preferred that digital-to-analog converter 116 be provided on-board the microprocessor chip. Hence, software field modulator 114 provides the ac component at node 118.

The signal from digital-to-analog converter 116 is fed to voltage-to-current amplifier 120, the output of which drives magnetic field generating coils 112 in the desired manner. Hence, the composite field is held substantially constant despite changes in the ambient component.

While several arrangements of power sources are suitable, it is preferred that power supply 122 be provided to power magnetic field sensor amplifier 106, microprocessor 100 and magnetic field sensor 104, the latter via bias circuitry 124. A separate power source 126 is preferred for voltage to current amplifier 120.

Figure 8:
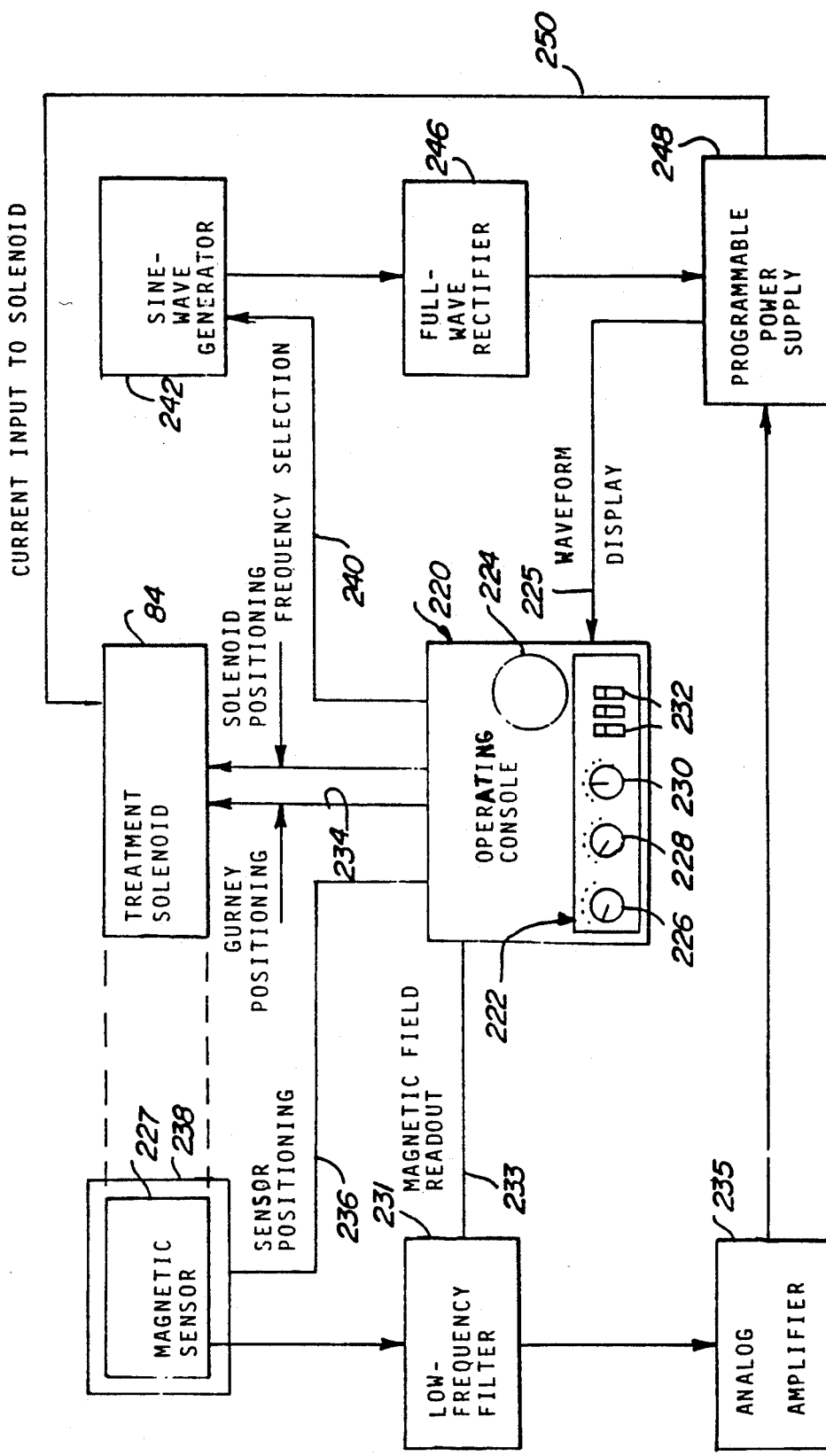
FIG. 8 is a block diagram of the circuitry of one embodiment of the present invention for use in systemic treatment.

Referring now to FIG. 8, a block diagram is shown which is preferred for use in connection with systemic treatment apparatus 80. Operating console 820 forms the control center for operating systemic treatment apparatus 80. The console is comprised of a plurality of control elements 222 and a visual display device 224 for monitoring the wave form display of the solenoid current signal 225. The plurality of control elements 222 include a gurney positioning dial 226 for controlling the lateral movement of the gurney platform. Magnetic field sensor adjusting dial 228 allows the operator to selectively position the magnetic field sensor 227 within the center of treatment solenoid 84. The treatment structure rotating dial 230 allows the operator to rotate the concentric solenoid and platform 88 in the horizontal plane in that embodiment where a supporting stand or turntable (not shown) is provided. This horizontal movement allows the solenoid coil to be positioned so that it may compensate for undesired local magnetic fields. Switch elements 232 allow the operator to effect various other control tasks, such as turning the concentric solenoid current on or off, or setting the cyclotron resonance frequency for the ion of choice. Each of the above mentioned dials and switch elements produce signals which go to various elements of systemic treatment apparatus 80 to accomplish the various functions described herein. The signal produced by the gurney positioning dial 226 leaves operating console 220 along cable 234 as does the signal produced by the treatment structure rotating dial 230. The signals 234 interface with various motors and other drive hardware to effect the positioning of platform 88 within solenoid 84, and the positioning of tube 82 with respect to the local magnetic field. Control line 236 transmits the signal developed by the magnetic field sensor adjusting dial 228 to a magnetic sensor positioning device 238 which allows the magnetic sensor 227 to be positioned at various locations within the center of the solenoid 84. After dials 226 through 230 and switches 232 have been set, systemic treatment apparatus 80 is ready for operation. The frequency which has been selected by the operator is output along line 240 to the sine wave generator 242. The sine wave generator 242 responds to the frequency selected in accordance with the principles of the present invention by generating a sinusoidal wave form which possesses one-half of the desired frequency with no DC offset. The signal is then sent from the sine wave generator 242 to a full-wave rectifier circuit 246. Rectifier 246 not only transforms the sinusoidal waveform produced by generator 242 to a rectified DC signal, it also has the effect of doubling the frequency of the output of the sine generator. The rectified signal is then sent from the full-wave rectifier 246 to the programmable power supply 248 where it is amplified to a sufficient power level which is necessary to develop a sufficiently strong magnetic field within the solenoid 84. The amplified signal is then sent from the programmable power supply 248 along cable 250 to solenoid 84. Solenoid 84 then converts the amplified current to a uniform magnetic field density within the concentric solenoid winding 84 along axis 50 shown in FIG. 5. Because of localized magnetic fields, the magnetic field, as it exists within the concentric solenoid winding, is not always absolutely predictable. Thus, magnetic sensor 227 is mounted in close proximity to the patient so that the magnetic flux density within solenoid 84 can be constantly monitored. A signal, which is proportional to the magnetic flux density within treatment solenoid 84, is output by the magnetic sensor 227 and then filtered by filter 231 to eliminate any undesired high-frequency elements. The output of low frequency filter 231 is then delivered to operating console 220 along cable 233 so that it can be displayed on the visual display device 224. The output of low frequency filter 231 is also sent to analog amplifier 235 so that it can be properly conditioned to be used within the programmable power supply 248. The programmable power supply 248 uses the output from analog amplifier 235 as a means for maintaining a uniform density magnetic field within the center of solenoid 84. This task may be performed within the programmable power supply by means of standard analog feedback techniques or may be accomplished by means of a digital processor.

Having fully described the apparatus of the present invention, including its manner of construction, operation and use, the method of the present invention will now be described. It is to be understood that this description of the method incorporates the foregoing discussion of the novel apparatus. In this aspect, the present invention provides a method of preventing and treating osteoporosis noninvasively. This is achieved in one embodiment by generating a fluctuating, directionally-oriented magnetic field which projects through the bone to be treated. The magnetic field generating means preferred for use is treatment apparatus 20 for topical application and systemic treatment apparatus 80 for systemic application which were previously described. The magnetic field so generated has a magnetic flux density of precisely controlled parameters which passes through the target bone region or, in the case of systemic application, through the entire patient parallel to a predetermined axis projecting through the bone or patient. As will be known by those skilled in art and as has been clearly explained, the local magnetic field to which the patient is subjected will have a component which is parallel to the predetermined axis and which thus aids or opposes the applied or generated magnetic field along the axis. At times, the local component may be zero. In the method of the present invention, the density of this combined magnetic flux, and more specifically the average non-zero value of the combined magnetic flux density, is controlled to provide a precise relationship between the flux density along the axis and the frequency of the applied magnetic field which is oscillating at a predetermined value. Most preferably this is accomplished by adjusting the intensity of the applied field to compensate for changes in the local field. Thus, in one embodiment, the present invention provides a method of preventing or therapeutically treating osteoporosis by creating a magnetic field which penetrates the target region of bone or the entire skeletal system and which has a predetermined relationship between frequency of oscillation and average flux density. The predetermined relationship or ratio of frequency-to-field intensity is determined with reference to the equation:

$$f_c/B = q/(2\pi m)$$

where $f_c$ is the frequency of the combined magnetic field along the predetermined axis in Hertz, B is non-zero net average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla.

In order to create this fluctuating magnetic field having the desired parameters, the composite magnetic field parallel to the predetermined axis is preferably repetitively monitored. As stated, this is preferably carried out with a Hall effect device or the like which produces an analog signal. This analog signal is periodically sampled by microprocessing means which then calculates the necessary frequency and/or magnitude of the applied magnetic field to maintain the preprogrammed, predetermined ratio previously described. Of course, it will now be understood that it is the combined magnetic flux which is sensed by the magnetic field sensor. The magnetic field generating means is used to adjust the magnitude of this composite field where appropriate.

In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintain the predetermined relationship of the present invention.

Hence, the method of the present invention includes the steps of creating and maintaining a predetermined relationship between the frequency of a fluctuating magnetic field to the flux density of the field. In particularly preferred embodiments, a frequency of 16 Hertz and an average flux density of $2.09 \times 10^{-5}$ Tesla are utilized. This combination of frequency and flux density is particularly useful in preventing or treating osteoporosis. Another preferred frequency and corresponding flux density which is useful for preventing or treating osteoporosis is 16 Hertz and $1.27 \times 10^{-5}$ Tesla.

In a preferred embodiment of the method of the present invention, the ratio of frequency-to-flux density is determined by selecting a preselected ion present in the biological fluids associated with bone cells and tissue which is to be treated by the present invention and tuning the fluctuating composite magnetic flux density to the specific cyclotron resonance frequency for the ion. The preferred ions for preventing and treating osteoporosis are $Ca^{++}$ and $Mg^{++}$. Other ions which may be useful in the present invention are set forth in the following table:

Hydrogen, $H^+$
Lithium, $Li^+$
Sodium, $Na^+$
Fluorine, $F^-$
Chlorine, $Cl^-$
Strontium, $S^{2+}$
Bicarbonate, $HCO^-_3$ Hence, in addition to the apparatus of the present invention, the present invention provides a method for preventing and treating osteoporosis which includes the steps of creating a fluctuating magnetic field of predetermined frequency and flux density along an axis projecting through a predetermined volume and positioning a region of bone in which osteoporosis is to be prevented or region of bone afflicted with osteoporosis which is to be therapeutically treated within this predetermined space such that it is exposed to the fluctuating magnetic field. The predetermined parameters of the fluctuating magnetic field are determined by measuring the net average value of the combined magnetic flux density parallel to the predetermined axis through the bone, where the combined magnetic field is the sum of the local magnetic field along the predetermined axis and the applied magnetic field. The frequency and/or magnitude of the applied magnetic flux density is then adjusted to produce a combined magnetic field along the axis having a predetermined ratio of frequency-to-flux density. This predetermined ratio prevents osteoporosis and brings about a reversal of osteoporosis such that bone mass is increased and porosity is decreased. The target bone region, or the entire patient in systemic application, is exposed to the fluctuating magnetic field for a duty cycle and a period of time sufficient to produce the desired effect.

In still another embodiment of the present invention, an animal model is produced for the study of bone diseases such as osteoporosis. Accordingly, apparatus such as treatment apparatus 20 or systemic treatment apparatus 80 is utilized to produce bone resorption in an experimental animal such as a laboratory rat or rabbit. This is achieved by tuning for the ion $K^+$ among others and exposing the subject animal to the composite field in accordance with the previous explanation of cyclotron resonance tuning. It is believed that exposure for about 100 hours will produce a significant degree of bone resorption in the affected bone region or throughout the skeletal system where systemic application is provided.

The following examples are provided to further described and illustrate the present invention and are in no way intended to limit the scope of the appended claims.

EXAMPLE A

Freshly-laid fertile white leghorn chicken eggs were obtained and were incubated in a 100% humidified atmosphere at 40 degrees C. for 8 days. Then the eggs were then removed and candled. For each run of the experiments, 26 eggs with normal-appearing embryos were selected.

The eggs were opened, and the embryos were removed to a sterile Petri dish. Abnormal embryos were discarded. The femurs of the embryos' legs were removed by blunt dissection with forceps and transferred in right-left pairs to sterile gauze squares moistened with Hanks' Balanced Salt Solution (HBSS) in another sterile dish. From this dish, pairs were removed to squares of dry, sterile unbleached muslin, where they were rolled back and forth under a dissecting microscope until adhering tissue was removed. This procedure left the bones stripped of all tissue except the perichondrium/periosteum. Tissue removal was confirmed microscopically. The right leg of each pair was reserved as a control and the left became an experimental subject. The length of each femur was measured with a sterile metric vernier caliper and recorded.

The isolated femurs prepared for culture by the above method were placed into the wells of 12-well culture plates (Linbro). A small triangular type 316 stainless steel mesh screen was placed in each well. The corners had been folded under to lift the mesh slightly away from the bottom of the plate and to allow for media circulation. A sterile triangle of thoroughly washed ordinary lens paper was placed atop the mesh screen, and the femurs were oriented in orthogonally positioned pairs on the lens paper. The first femur into the well was placed parallel to the base of the triangle of lens tissue, while the next was placed perpendicular to it in the center of the triangle. Thus, each femur could be identified later, since the wells were also numbered sequentially.

As each well was completed, it was given a 0.5 ml aliquot of sterile $BGJ_6$ medium (Fitton-Jackson modification, GIBCO) containing antibiotics and antimycotics (GIBCO). This amount was just sufficient to saturate the lens tissue and produce a meniscus of medium over the explanted femurs. As soon as each plate was completed, it was covered and placed in either a control or experimental position within a water-jacketed $CO_2$ incubator containing a 100% humidified atmosphere of 5% $CO_2$ in air at 40 degrees C. Subsequent culture consisted of seven days in the incubator, with fresh medium every other day.

The dishes containing the left femurs were placed between 15 cm diameter Helmholtz coils according to the method of the present invention. The exact field strength depended on the ion selected. A Beckman FG-2 function generator supplied a 16 Hz ac sine wave along the coil axis, whose amplitude was set at 30 microtesla, peak-to-peak. The frequency of the signal was checked with a Beckman UC-10 frequency counter calibrated against an NBS-referrable source. The amplitude of the ac and static magnetic fields was checked with a single-axis fluxgate magnetometer (Schonstedt Instruments Model 2200-DS). Ac amplitude was read by feeding the analog output from the magnetometer to a Tektronix 204 A oscilloscope. Given the 16 Hz ac field, the static field varied according to the q/m ratio of the ion. For Calcium, B was 20.9 microtesla. For Magnesium, 12.7 microtesla satisfied resonance conditions for B. For the combined treatment, B was set at 20.9 microtesla and the ac frequency was raised to 80 Hz. As will be seen readily by calculation, this represents the fifth harmonic for calcium and the third harmonic for magnesium resonance. Using this combination, a simultaneous stimulation for both ions was achieved.

The control cultures were maintained in the same chamber as the experimentals, but were shielded from the magnetic fields. The ac magnetic field strength to which the control femurs were subjected was at least two orders or magnitude less than the experimentals (no greater than 0.3 microtesla, peak-to-peak). The ambient 60 Hz magnetic field in the chambers was less than 0.1 microtesla.

At the end of the experiment, the medium was removed from each well of the dishes, and was replaced with an equal amount of Millonig's Neutral Buffered Formalin. After 24 hours to allows for fixation and shrinkage, the femurs were removed gently from the lens paper and the length and central disphyseal diameters were measured with the same pair of vernier calipers used previously. The measurements were made and recorded in a blind manner. The femurs were then returned to the wells, with a small paper divider to keep them separate and identifiable. They were then decalcified and embedded through alcohols and benzene into 54 degrees paraplast, then cut longitudinally at 8 microns and stained with Mayer's Haematoxylin and Eosin.

The sections were examined under a light microscope (Olympus CH-2) and measurements of the diaphyseal collar length and thickness were made with an ocular micrometer. An assessment of the degree of maturation was also made, together with notes on the histological appearance of the bones. A Student's T-test of the paired experimentals and controls was performed. Each experiment was performed in duplicate, so that there were 96 bones in each ionic group, 48 experimentals and 48 controls. These numbers presented in Table I gave clear statistical inferences:

TABLE I

| Results of Check Femur Tests | | | |
|---|---|---|---|
| Category of Measurement | Ca | Mg | Ca/Mg |
| 1. Bone Length (mm) | 9.4* | 8.4* | 8.7* |
| S.D. | 0.75 | 0.7 | 0.8 |
| Controls | 8.15 | 7.8 | 7.8 |
| S.D. | 0.5 | 0.6 | 0.7 |
| 2. Bone Diameter (mm) | 1.24* | 1.04* | 1.03* |
| S.D. | 0.13 | 0.06 | 0.12 |
| Controls | 0.88 | 0.79 | 0.70 |
| S.D. | 0.11 | 0.07 | 0.08 |
| 3. Length/Diameter | 7.8* | 8.4* | 9.1* |
| S.D. | 1.0 | 0.8 | 0.7 |
| Controls | 9.5 | 10.2 | 11.1 |
| S.D. | 1.3 | 0.6 | 1.03 |
| 4. Collar Length (mm) | 2.27* | 1.76* | 2.31* |
| S.D. | 0.38 | 0.72 | 0.53 |
| Controls | 1.67 | 1.09 | 1.16 |
| S.D. | 0.19 | 0.26 | 0.23 |
| 5. Collar Thickness (mm) | 0.043* | 0.035* | 0.045* |
| S.D. | 0.012 | 0.012 | 0.014 |
| Controls | 0.022 | 0.025 | 0.025 |
| S.D. | 0.007 | 0.006 | 0.008 |

*$p < .01$ compared to paired control value

The histological appearance of the controls did not vary from run to run. The picture they presented was essentially normal. The ends of the bones were composed of relatively condensed and cellular hyaline cartilage. The diaphyseal collar was quite thin, but well-ossified, while the central diaphyseal region had modestly hypertrophied chondrocytes, with a few pyknotic nuclei, but little or no calcification of the cartilage matrix.

When the fields were tuned to calcium ions, the length of the bones was significantly ($p<0.01$) increased (+15%) as compared to controls. The bones were also significantly more robust (+22%) (diameter was increased as a function of length). The bone diameter (+41%), diaphyseal collar length (+36%), and diaphyseal collar thickness (+95%) were also increased significantly ($p<0.01$).

The histological picture was also altered markedly. The general appearance was of considerably advanced maturation of the bone, with extensive hypertrophy of all chondrocytes but those at the ends of the bones. The central diaphyseal region showed extensive calcification of the cartilage matrix, and many of the central diaphyseal chondrocytes had pyknotic nuclei.

The results with magnesium tuning appeared similar to those with calcium. Bone length and especially diameter were significantly ($p<0.01$) increased (+8% and +32%). The bones were also considerably more robust (+20%). The increase in collar length was especially large, (+61%) as compared to controls, contrasted with only a 36% increase for calcium tuning. Collar thickness was also markedly increased (+40%), (p<0.01) though not as much as for calcium.

Histologically, the picture for magnesium was quite different than for calcium. Rather than presenting advanced maturation, the magnesium-treated bones merely seemed to evidence overall enlargement. The cellular picture looked similar to controls. Everything appeared to have been increased, as though overall growth has been stimulated.

When both calcium and magnesium ions were subjected to CR conditions, the results were essentially a combination of those for calcium and magnesium separately. The bones were significantly (p<0,01) lengthened (+12%) and thickened, (+47%) and the diaphyseal collar length (+99%) and thickness (+80%) were also increased (p<0.01). Robustness increased by 22%.

Histologically, the bones were, as with calcium, advanced with respect to calcification, the central diaphyseal region showing marked calcification. However, the degree of this effect was slightly less than with calcium stimulation alone. The rest of the bone showed generalized enlargement, as with magnesium tuning.

EXAMPLE B

Several studies using fibula ostectomies in skeletally mature rabbits were also performed.

Skeletally mature (2.5 Kg) New Zealand White rabbits of mixed sex were divided into groups of six animals each, and anaesthetized. After anaesthesia, both legs were shaved laterally and painted with betadyne solution. An incision was made 1 cm caudal to the knee, extending for 2.5 cm. The muscles of the anterior and peroneal compartments were separated to expose the fibula. The periosteum was split and reflected from the bone. On the right, the periosteum was allowed to return to the place. These bones served as the sham operations. On the left, a 1 cm piece of the fibula was removed from the bone, beginning approximately 1 cm cranial to the union of fibula and tibia. The periosteum was allowed to return. These bones served as the operated series. The wounds of both sides were then closed in layers, ending with stainless steel sutures. The animals were then returned to their cages for recovery.

Eighteen animals were placed in cages which lay between pairs of Helmholts coils, according to the method of the present invention. They were stimulated for ½ hour per day. Six of the animals then received combined ac and static magnetic fields tuned to calcium using the method of the present invention. The static field was 40 microtesla, the ac sine wave field was 30 microtesla peak-to-peak, and the ac frequency was 30.6 Hz. Six more animals received fields tuned to magnesium ions. The static field was again 40 microtesla, the ac field was 30 microtesla peak-to-peak, and the ac frequency was 50.5 Hz. A final six animals received the combined field tuned for calcium and magnesium simultaneously. The B-field was set at 40 microtesla, the ac field strength was set at 30 microtesla peak-to-peak, and the ac frequency was 153 Hz. This set of conditions, as may be readily seen, represents the fifth harmonic for calcium and very nearly the third harmonic for magnesium (151.5 Hz). The final six animals received no magnetic field stimulation, and served as controls.

After one month of stimulation, the rabbits were removed from the cages and sacrificed by $CO_2$ inhalation. The legs were disarticulated and removed. A-P radiographs were taken of each leg, and the muscle tissue was then stripped from the bones. The diameters of the fabellae and callus were measured from the radiographs with a digital micrometer. The fibulas were removed and clamped into a cantilever bending testing jig. Each femur was then bent in the A-P axis by moving the bone with a micrometer screw against the tip of the force transducer positioned 1.5 cm above the tip of the clamp jaws. This length of bone included the ostectomy site. The bones were bent 1 mm, and the force required to produce the bending was recorded by an oscillograph connected to a computer, which produced on-screen graphs of force vs. deflection. The F-D ratios of operated vs. sham-operated sides were compared. The results of the tests may be seen below.

The results of the tests are presented graphically in Table II:

TABLE II

| | OSTECTOMY RESULTS | | |
|---|---|---|---|
| Condition | Fabellar Diam. (mm) | Callus Diam. (mm) | F–D Ratio |
| Control | 2.73 +− .39 | 2.81 +− .52 | .57 +− .26 |
| Calcium | 2.98 +− .45 | 3.63 +− .56* | 1.84 +− 1.31# |
| Magnesium | 4.04 +− .42# | 4.18 +− .97# | 1.04 +− .73* |
| Ca/Mg 5/3 | 3.77 +− .49# | 3.99 +− .84# | 1.88 +− .74# |

*$p < .05$
$p < .01$

From these results, it is obvious that the application of fields tuned to cyclotron resonance conditions for calcium according to the method of the present invention materially increases mineralization (stiffness) and callus formation, without significantly influencing normal osteogenesis (fabellar diameter.) Magnesium tuning very markedly influences growth and callus formation, but has less of an effect upon mineralization. Combining calcium and magnesium stimulation produces at the cellular level the growth and osteogenetic effects of magnesium with the mineralization effects of calcium, thereby providing the means for the prevention and treatment of osteoporosis.

What is claimed is:

1. A method for controlling osteoporosis, comprising the steps of:
    positioning a magnetic field generating means adjacent a region of bone affected by osteoporosis, said region of bone being subject to an ambient static magnetic field;
    generating an applied fluctuating magnetic field with said magnetic field generating means and applying said magnetic field along an axis through said region of bone to combine said applied magnetic field with a component of said ambient magnetic field also extending along said axis to create a total magnetic field along said axis;
    sensing the magnitude of said total magnetic field, along said axis including said component of said ambient static magnetic field; and
    controlling said applied fluctuating magnetic field and the magnitude of said applied fluctuating magnetic field to create and maintain a ratio of the frequency of said fluctuation to the magnitude of the total magnetic field along said axis to control osteoporosis in said bone region.

2. The method for controlling osteoporosis recited in claim 1, further comprising the steps of monitoring the magnitude of the total magnetic field along said axis and changing the frequency of said applied fluctuating magnetic field to maintain said ratio as the magnitude of the total magnetic field along said axis changes due to changes in the ambient static magnetic field component.

3. The method for controlling osteoporosis recited in claim 1, further comprising the steps of monitoring the magnitude of the total magnetic field along said axis and changing the magnitude of the applied field to maintain said ratio as the magnitude of the total magnetic field along said axis changes due to changes in the ambient static magnetic field component.

* * * * *

UNITED STATES PATENT AND TRADEMARK OFFICE
CERTIFICATE OF CORRECTION

PATENT NO. : 5,267,939
DATED     : 12/7/93
INVENTOR(S) : Liboff et al.

It is certified that error appears in the above-identified patent and that said Letters Patent is hereby corrected as shown below:

Col. 1, lines 41-42, "vitamin B" should read "vitamin D".

Col. 2, line 15, "homeostacis" should read "homeostasis".

Col. 4, line 57, "prevention treatment" should read "prevention or treatment".

Col. 13, line 6, "frequency" should read "frequent".

Signed and Sealed this

Nineteenth Day of July, 1994

Attest:

BRUCE LEHMAN

Attesting Officer    Commissioner of Patents and Trademarks